United States Patent
Hara et al.

(10) Patent No.: US 12,318,472 B2
(45) Date of Patent: Jun. 3, 2025

(54) PLANT-DERIVED PROTEOGLYCAN AND APPLICATION THEREOF

(71) Applicant: NOF CORPORATION, Tokyo (JP)

(72) Inventors: Masao Hara, Tsukuba (JP); Mamoru Tsuchida, Tsukuba (JP)

(73) Assignee: NOF CORPORATION, Tokyo (JP)

( * ) Notice: Subject to any disclaimer, the term of this patent is extended or adjusted under 35 U.S.C. 154(b) by 539 days.

(21) Appl. No.: 17/637,568

(22) PCT Filed: Sep. 24, 2019

(86) PCT No.: PCT/JP2019/037350
§ 371 (c)(1),
(2) Date: Feb. 23, 2022

(87) PCT Pub. No.: WO2021/059344
PCT Pub. Date: Apr. 1, 2021

(65) Prior Publication Data
US 2022/0287954 A1 Sep. 15, 2022

(51) Int. Cl.
| | |
|---|---|
| *A61K 8/9789* | (2017.01) |
| *A23L 33/105* | (2016.01) |
| *A61K 38/02* | (2006.01) |
| *A61Q 19/00* | (2006.01) |
| *C08B 37/00* | (2006.01) |

(52) U.S. Cl.
CPC .......... *A61K 8/9789* (2017.08); *A61Q 19/00* (2013.01); *C08B 37/00* (2013.01); *A23L 33/105* (2016.08); *A61K 38/02* (2013.01)

(58) Field of Classification Search
CPC ........... C08L 5/00; A61K 8/645; A61K 36/48; A61K 8/9789; A61K 38/02; A61K 2236/00; C08B 37/0003; C08B 37/00; C08B 37/0087; A61Q 19/00; A23L 33/105
USPC ........................................................ 426/573
See application file for complete search history.

(56) References Cited

U.S. PATENT DOCUMENTS
2003/0211077 A1 11/2003 An et al.

FOREIGN PATENT DOCUMENTS
| | | |
|---|---|---|
| JP | 2004-502703 A | 1/2004 |
| JP | 2018-168263 A | 11/2018 |

OTHER PUBLICATIONS

Osman et al., "Characterization of Gum Arabic Fractions Obtained by Anion-Exchange Chromatography," *Phytochemistry*, 38(2): 409-417 (1995).
Japan Patent Office, International Search Report in International Patent Application No. PCT/JP2019/037350 (Dec. 3, 2019).

*Primary Examiner* — Subbalakshmi Prakash
(74) *Attorney, Agent, or Firm* — Leydig, Voit & Mayer, Ltd.

(57) ABSTRACT

The present invention relates to a plant proteoglycan obtained from gum arabic obtained from a trunk or branch of Acacia plant (Acacia Senegal Willdenow or Acacia Seyal Delile), having a weight average molecular weight of 900,000-3,500,000, and having a total aldehyde content of not more than 2.0 μmol equivalent/g. A plant proteoglycan having physiological activity equal to or higher than that of animal proteoglycan can be provided by the present invention.

1 Claim, 4 Drawing Sheets

[Fig. 1]
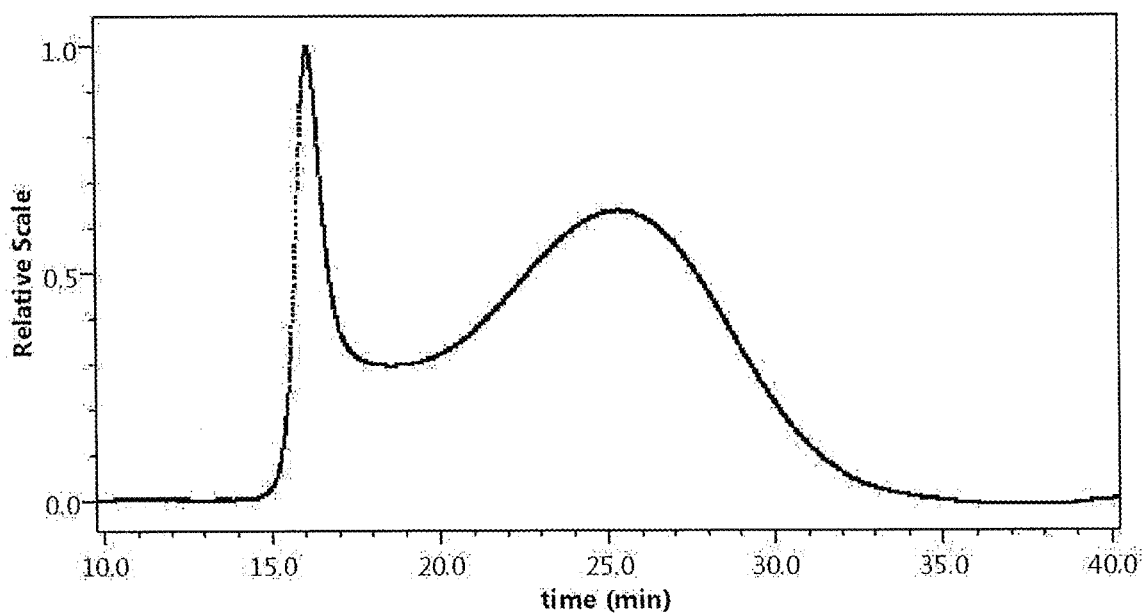
[Fig. 2]
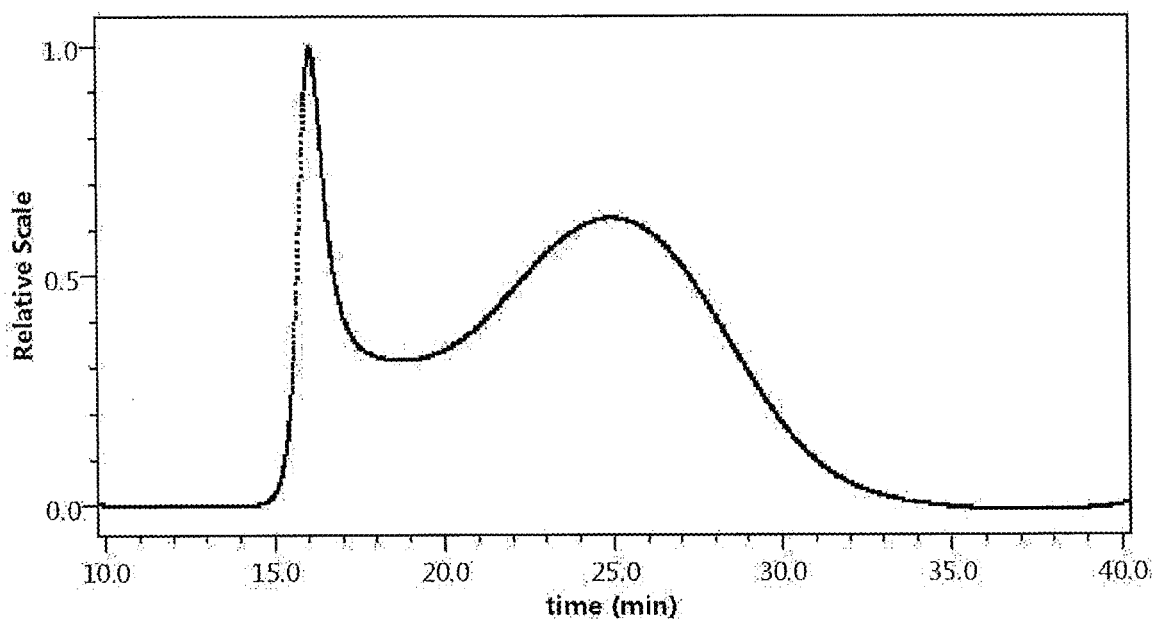

[Fig. 3]
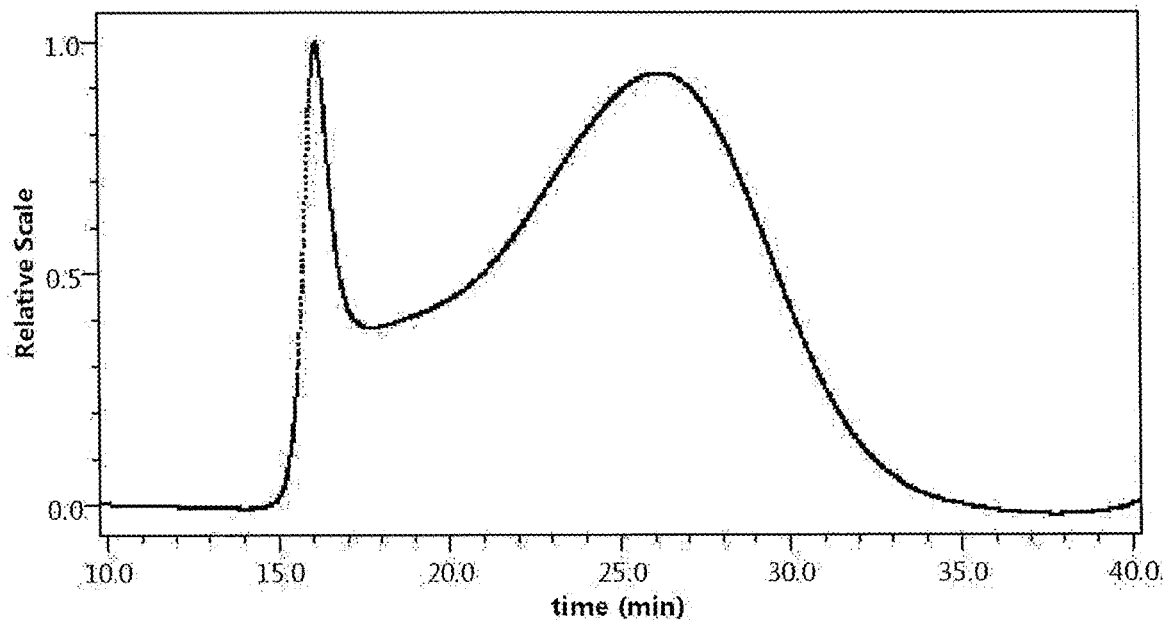
[Fig. 4]
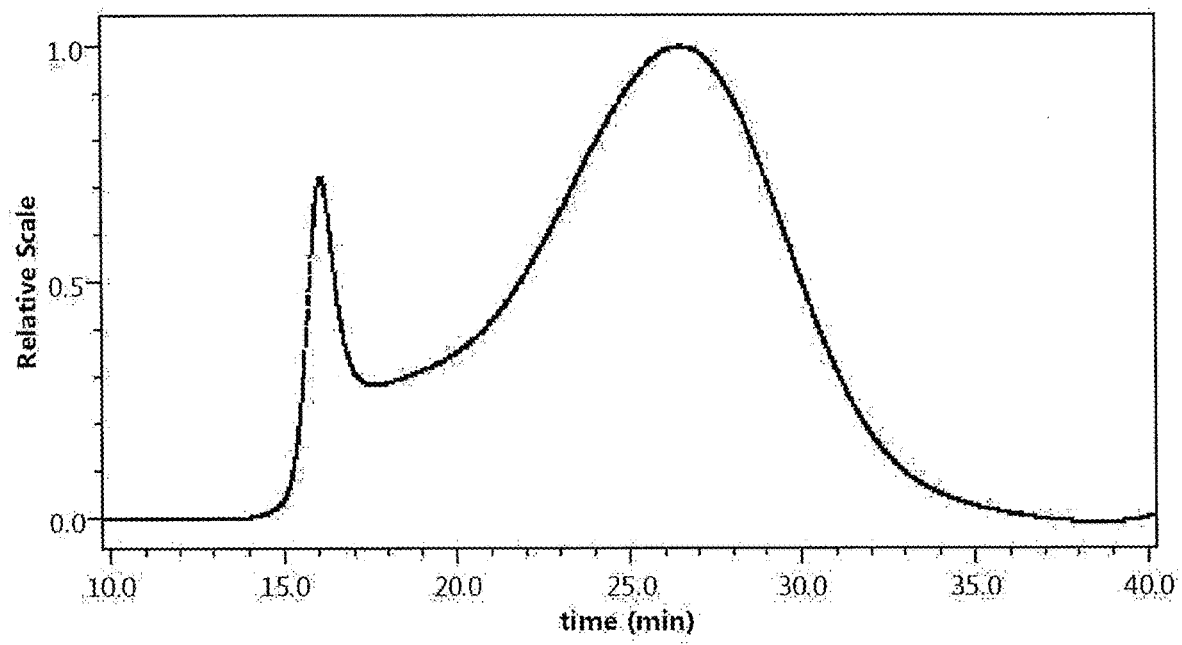

[Fig. 5]
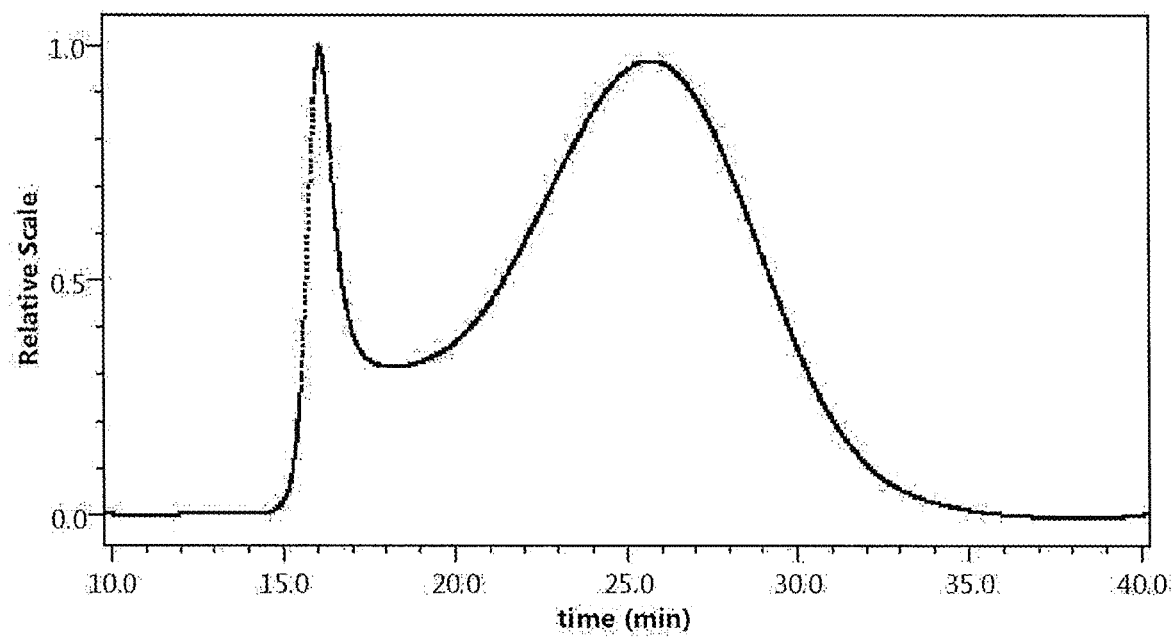
[Fig. 6]
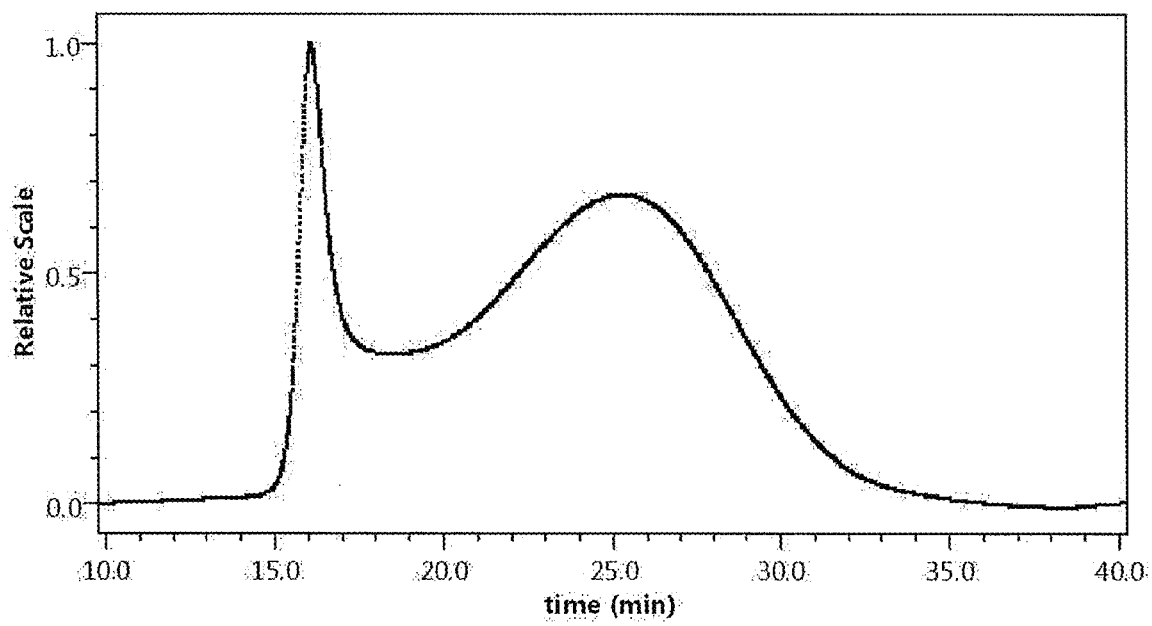

[Fig. 7]
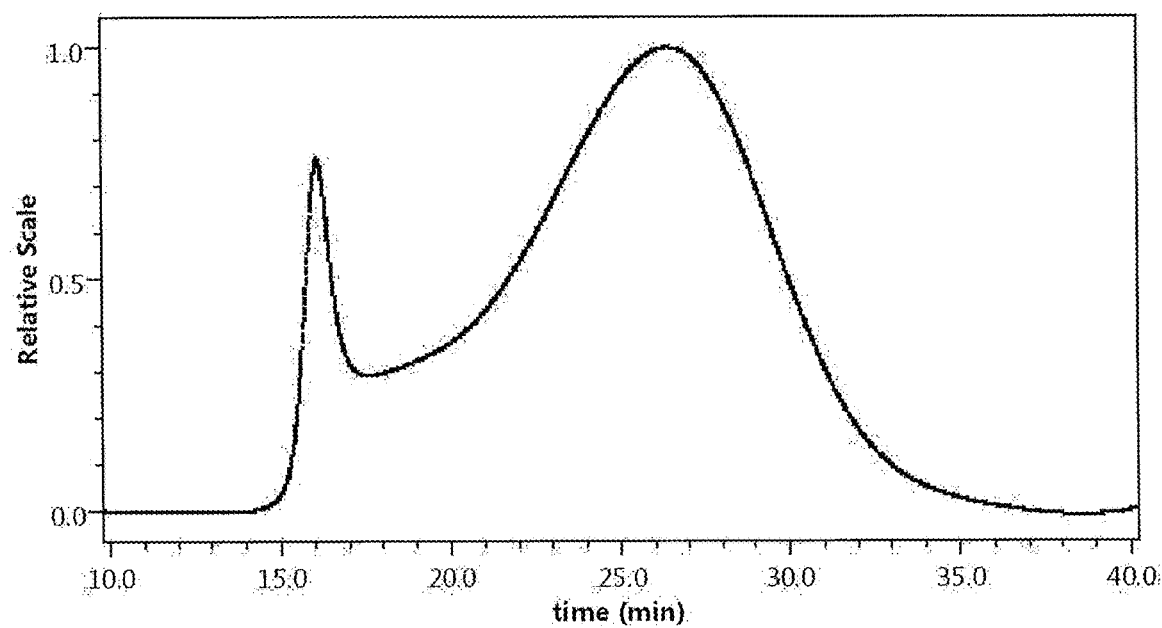
[Fig. 8]
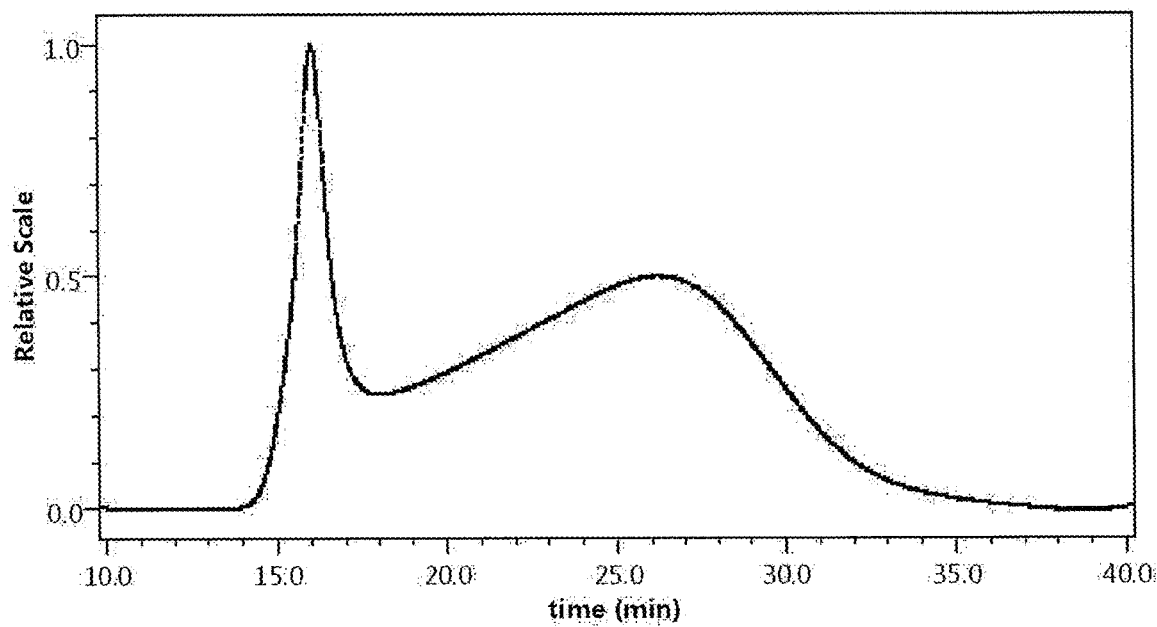

PLANT-DERIVED PROTEOGLYCAN AND APPLICATION THEREOF

TECHNICAL FIELD

The present invention relates to plant proteoglycan. More particularly, the present invention relates to plant proteoglycan having physiological activity equal to or higher than that of animal proteoglycan.

BACKGROUND ART

In recent years, it has been clarified that glycoprotein has remarkable physiological activity. Animal proteoglycan, which is one of glycoproteins, is a generic term for compounds in which plural glucosaminoglycan sugar chains and one core protein are covalently bonded, and it is widely used as a cosmetic component due to its high moisture retention and cell proliferation promoting action. As the animal proteoglycan, for example, those derived from salmon nasal cartilage, shark fin cartilage and squid head cartilage are known. However, since animal proteoglycan is a substance present in a trace amount in cartilage, there is a problem of high production cost. In the cosmetics market and the food market, moreover, since plant-derived components have a better image than animal-derived components, it has been demanded to replace animal proteoglycans with plant-derived components.

Plants include arabinogalactan protein with a structure similar to that of animal proteoglycan. Arabinogalactan protein is a generic term for compounds in which an arabinogalactan sugar chain and a core protein are covalently bonded, and is a proteoglycan. Emulsifying property is known as an effect of arabinogalactan protein (Non Patent Literature 1). Gum arabic is a mixture of arabinogalactan protein, arabinogalactan, and glycoprotein (Non Patent Literature 1). Gum arabic is a sap recovered from the exudate of Acacia. Gum arabic is widely applied to cosmetic use because it has a thickening action and an emulsifying action, and about 2,000 tons are imported into Japan every year. Gum arabic is easily available in Japan and has made many achievements in terms of safety, and the like since it is registered as a cosmetic material in "the Japanese Standards of Quasi-drug Ingredients 2006", and as a food material in "Japan's Specifications and Standards for Food Additives 8th Edition". Thus, gum arabic can be said to be useful as a raw material for plant proteoglycan.

CITATION LIST

Patent Literatures

[PTL 1]
JP-A-2000-166489
[PTL 2]
JP-B-05-41642
[PTL 3]
JP-B-3-16169

Non Patent Literature

[NPL 1]
Carbohydrate Research, 246(1993) p. 303-318

SUMMARY OF INVENTION

Technical Problem

Patent Literature 1 shows that gum arabic becomes a modified gum arabic with enhanced emulsifying power by heating the gum arabic at 60° C.-140° C. for 30 min or longer. Patent Literature 2 shows that the viscosity of gum arabic increases markedly by a treatment with a cation exchange resin and further heat denaturation at 100° C.-160° C. The modified gum arabic had an increased weight average molecular weight as compared with the gum arabic before modification, and was expected to have superior bioactivity. According to the research by the present inventors, the modified gum arabic obtained by this method has a high total aldehyde content and therefore has low physiological activity. In addition, this modified gum arabic has a sticky feeling because the weight average molecular weight is too high, and shows a poor sense of use when applied to the skin, and generates an odor. It was found that, because of these, the modified gum arabic cannot be a substitute for animal proteoglycan.

Patent Literature 3 shows that treatment of gum arabic with a cation exchange resin improves emulsification stability. According to the research by the present inventors, it was found that the purified gum arabic obtained by this method does not contain a sufficient amount of arabinogalactan protein, and therefore has low physiological activity, and cannot be a substitute for animal proteoglycan.

Therefore, plant proteoglycan having physiological activity equal to or higher than that of animal proteoglycan, superior in the sense of use when applied to the skin, and free of an odor problem has not been found yet.

The present invention has been made in view of the above-mentioned situation, and aims to provide plant proteoglycan having physiological activity equal to or higher than that of animal proteoglycan, superior in the sense of use when applied to the skin, and free of an odor problem.

Solution to Problem

The present inventors conducted intensive studies in an attempt to solve the above-mentioned problem, and found that plant proteoglycan having physiological activity equal to or higher than that of animal proteoglycan can be obtained from gum arabic obtained from the trunk or branch of Acacia plant (Acacia Senegal Willdenow or Acacia Seyal Delile), which resulted in the completion of the present invention.

That is, the present invention provides the following.
[1] A plant proteoglycan obtained from gum arabic obtained from a trunk or branch of Acacia plant (Acacia Senegal Willdenow or Acacia Seyal Delile), having a weight average molecular weight of 900,000-3,500,000, and having a total aldehyde content of not more than 2.0 µmol equivalent/g.
[2] A method for producing the plant proteoglycan of [1], comprising the following step (A) and step (B):
  step (A): a step of preparing a gum arabic aqueous solution having a concentration of 0.5% (w/w)-40% (w/w)
  step (B): a step of subjecting the gum arabic aqueous solution to a strongly basic porous type I anion exchange resin and a strongly acidic cation exchange resin.
[3] A cell proliferation promoter comprising the plant proteoglycan of the above-mentioned [1].
[4] A cosmetic comprising the plant proteoglycan of the above-mentioned [1].
[5] A cosmetic comprising the cell proliferation promoter of the above-mentioned [3].

Advantageous Effects of Invention

The plant proteoglycan of the present invention has physiological activity equal to or higher than that of known animal proteoglycan, and exhibits a superior moisturizing effect and a cell proliferation promoting effect on the human skin. In addition, when used as a cosmetic material, it can realize a cosmetic having a superior moisturizing effect and a cell proliferation promoting effect, and also a good image, since it is derived from a plant.

BRIEF DESCRIPTION OF DRAWINGS

FIG. 1 shows a chromatogram obtained by size exclusion chromatography of a purified product obtained by treating gum arabic with the strongly basic porous type I anion exchange resin and the strongly acidic cation exchange resin in Example 1.

FIG. 2 shows a chromatogram obtained by size exclusion chromatography of a purified product obtained by treating gum arabic with the strongly basic high porous type I anion exchange resin and the strongly acidic cation exchange resin in Example 2.

FIG. 3 shows a chromatogram obtained by size exclusion chromatography of a purified product obtained by treating gum arabic with the strongly basic high porous type I anion exchange resin and the strongly acidic cation exchange resin in Example 3.

FIG. 4 shows a chromatogram obtained by size exclusion chromatography of the gum arabic in Comparative Example 1.

FIG. 5 shows a chromatogram obtained by size exclusion chromatography of the desalted gum arabic in Comparative Example 2.

FIG. 6 shows a chromatogram obtained by size exclusion chromatography of a purified product obtained by treating gum arabic with the strongly basic porous type I anion exchange resin in Comparative Example 3.

FIG. 7 shows a chromatogram obtained by size exclusion chromatography of a purified product obtained by treating gum arabic with the strongly acidic gel type cation exchange resin in Comparative Example 4.

FIG. 8 shows a chromatogram obtained by size exclusion chromatography of the modified gum arabic in Comparative Example 8.

DESCRIPTION OF EMBODIMENTS

The present invention is explained according to the embodiments.

The "plant proteoglycan" in the present invention refers to a purified product obtained by removing mainly arabinogalactan and glycoprotein from gum arabic obtained from a trunk or branch of Acacia plant (Acacia Senegal Willdenow or Acacia Seyal Delile). The product contains an effective amount of an arabinogalactan protein component, and shows physiological activity equal to or higher than that of animal proteoglycan, which is due to a small content of an aldehyde compound that inhibits cell proliferation activity.

The plant proteoglycan of the present invention is defined by the weight average molecular weight measured by size exclusion chromatography, and the total aldehyde content. That is, it is characterized in that it satisfies the relationship where the weight average molecular weight of all peaks of the chromatogram obtained by size exclusion chromatography is 900,000-3,500,000, and the total aldehyde content measured using an aldehyde quantification kit is not more than 2.0 µmol equivalent/g.

The above-mentioned weight average molecular weight is preferably 1,000,000-3,000,000, more preferably 1,300,000-2,500,000, further preferably 1,500,000-2,000,000. The above-mentioned total aldehyde content is preferably 0.005 µmol equivalent/g-2.0 µmol equivalent/g, more preferably 0.005 µmol equivalent/g-1.7 µmol equivalent/g, further preferably 0.005 µmol equivalent/g-1.0 µmol equivalent/g, particularly preferably 0.005 µmol equivalent/g-0.8 µmol equivalent/g.

When the weight average molecular weight exceeds 3,500,000, the arabinogalactan protein component increases but the viscosity becomes high in some cases. Therefore, for example, when preparing a cosmetic using the plant proteoglycan of the present invention as a physiologically active ingredient, the handling may be difficult.

(SEC Measurement)

The weight average molecular weight can be determined by using gel permeation chromatography with a multi-angle light scattering detector and a differential refractive index detector that are connected online. In the present specification, the multi-angle light scattering detector is also referred to as "MALS detector", the differential refractive index detector is also referred to as "RI detector", and size exclusion chromatography using the multi-angle light scattering detector and differential refractive index detector connected online is referred to as "SEC measurement". According to the SEC measurement, the concentration of the object to be measured is calculated by the RI detector, and the absolute molecular weight is calculated by the MALS detector, whereby the weight average molecular weight can be determined.

The conditions of the SEC measurement employed in the present invention are as follows.

(i) system: Prominence HPLC system (manufactured by Shimadzu Corporation)

(ii) column: Superose 6 10/300 GL (manufactured by GE Healthcare Japan Corporation)

(iii) flow rate: 0.5 mL/min (iv) elution solvent: 0.2M aqueous sodium chloride solution (v) sample preparation: an analysis sample is diluted with an elution solvent, mixed for 1 hr, allowed to stand at 25° C. for 18 hr, insoluble matter is removed with a 0.45 µm cellulose acetate membrane filter, and the resulting solution is used as the measurement sample.

(vi) sample concentration: 0.4% (w/v)

(vii) sample liquid injection volume: 100 µL (viii) column oven temperature control: 30° C.

(ix) RI detector: Optilab T-rEX (temperature control 25° C.) (manufactured by WYATT Technology Corporation)

(x) MALS detector: DAWN HELEOS II 8+ (manufactured by WYATT Technology Corporation)

(xi) do/dc: 0.141

(xii) data plot model: Berry (Weight Average Molecular Weight)

The weight average molecular weight can be determined by treating the data obtained by the SEC measurement performed under the above-mentioned conditions by Astra Ver. 6.1.2.84 (manufactured by WYATT Technology Corporation) and the like. The weight average molecular weight in the present invention means the weight average molecular weight of all peaks above the straight line connecting the elution start point to the elution end point of the chromatogram obtained by SEC measurement using an RI detector and a MALS detector.

(Total Aldehyde Content)

The total aldehyde content can be determined using aldehyde quantification kit Amplite (Trade Mark) Colorimetric Aldehyde Quantitation Kit (Product Number 10051) (AAT Bioquest).

The measurement conditions of the total aldehyde content that are employed in the present invention are as follows.
  (i) detection container: 96-well clear bottom microplate
  (ii) standard solution preparation: Adlehyde Standard attached to the kit is diluted with a buffer aqueous solution attached to the kit.
  (iii) standard solution concentration: 0, 1, 3, 10, 30, 100, 300, 1,000 µM
  (iv) standard solution amount: 50 µL
  (v) sample preparation: measurement sample is diluted with ultrapure water.
  (vi) sample concentration: 5.0% (w/v)
  (vii) sample liquid amount: 50 µL
  (viii) reaction solution amount: 50 µL
  (ix) reaction conditions: 25° C., shading
  (x) reaction time: 30 min.
  (xi) measurement wavelength: 405 nm In the measurement of the total aldehyde content performed under the above-mentioned conditions, a calibration curve is drawn from the absorbance of the obtained standard solution. By applying the absorbance of the obtained sample to the calibration curve, the total aldehyde content per 1 g of the sample can be determined.

The weight average molecular weight means the proportion of the active ingredient arabinogalactan protein (high molecular weight component) in a sample, and the total aldehyde content means a residual degree of an aldehyde compound in a purified product that adversely influences the physiological activity.

The plant proteoglycan of the present invention satisfies the relationship between a weight average molecular weight of 900,000-3,500,000, and a total aldehyde content of not more than 2.0 µmol equivalent/g. That is, since it has a less residual amount of an aldehyde compound that adversely influences physiological activity, and contains a sufficient amount of arabinogalactan protein (the below-mentioned Examples 1-3), superior results are obtained in any of cell proliferation activity effect, moisture retention and sensory test results, and physiological activity equal to or higher than that of animal proteoglycan can be afforded, as is clear from the results shown below [Evaluation test] (see Table 1).

The below-mentioned Comparative Examples 1, 2 are drawn to unpurified gum arabic. They fail to satisfy the weight average molecular weight of not less than 900,000, and contain a large amount of an aldehyde compound that adversely influences the physiological activity. As a result, the physiological activities thereof are far lower than that of animal proteoglycan, and it cannot provide the plant proteoglycan of the present invention (see Table 1).

The below-mentioned Comparative Example 3 is drawn to a purified product obtained by treating gum arabic with a strongly basic porous type I anion exchange resin, and having a weight average molecular weight of 1,420,000. Due to a high residual amount of an aldehyde compound that adversely influences the physiological activity, it does not have physiological activity equal to or higher than that of animal proteoglycan, permits the odor of the resin to transfer to purified products, shows poor sense of use when applied to the skin, and cannot be the plant proteoglycan of the present invention (see Table 1).

The below-mentioned Comparative Example 4 is drawn to a purified product obtained by treating gum arabic with a strongly acidic gel type cation exchange resin. It contains a less residual amount of an aldehyde compound that adversely influences the physiological activity, but does not satisfy a weight average molecular weight of not less than 900,000, and does not contain a sufficient amount of arabinogalactan protein. As a result, it does not have physiological activity equal to or higher than that of animal proteoglycan, and cannot be the plant proteoglycan of the present invention (see Table 1).

The below-mentioned Comparative Example 5 is drawn to a purified product obtained by treating gum arabic with a strongly basic gel type I anion exchange resin and a strongly acidic cation exchange resin. It contains a less residual amount of an aldehyde compound that adversely influences the physiological activity, but does not satisfy a weight average molecular weight of not less than 900,000, and does not contain a sufficient amount of arabinogalactan protein. As a result, it does not have physiological activity equal to or higher than that of animal proteoglycan, and cannot be the plant proteoglycan of the present invention (see Table 1).

The below-mentioned Comparative Example 6 is drawn to a purified product obtained by treating gum arabic with a strongly basic porous type II anion exchange resin and a strongly acidic cation exchange resin. It contains a less residual amount of an aldehyde compound that adversely influences the physiological activity, but does not satisfy a weight average molecular weight of not less than 900,000, and does not contain a sufficient amount of arabinogalactan protein. As a result, it does not have physiological activity equal to or higher than that of animal proteoglycan, and cannot be the plant proteoglycan of the present invention (see Table 1).

The below-mentioned Comparative Example 7 is drawn to a purified product obtained by treating gum arabic with a strongly basic porous type I anion exchange resin and a weakly acidic cation exchange resin, and having a weight average molecular weight of 1,420,000. Due to a high residual amount of an aldehyde compound that adversely influences the physiological activity, it does not have physiological activity equal to or higher than that of animal proteoglycan, and cannot be the plant proteoglycan of the present invention (see Table 1).

The below-mentioned Comparative Example 8 is drawn to gum arabic modified by the method described in Patent Literature 1, namely, the method of heating gum arabic at 60° C.-140° C. for 30 min or longer, which shows a cell proliferation activity effect lower than that of the unpurified gum arabic of Comparative Example 1 or 2 (see Table 1). It has a weight average molecular weight of 3,990,000, and contains many high molecular weight components. Since the aldehyde compound is generated by heating the gum arabic, the content of the aldehyde compound is high. The aldehyde compound inhibits the physiological activity, which in turn prevents effective physiological activity from being exhibited. In addition, since the weight average molecular weight is too high, a sticky feeling occurs and the sense of use when applied to the skin is poor.

(Material)

Gum arabic which is used as the material of the plant proteoglycan of the present invention is a natural exudate obtained from a trunk or branch of Acacia Senegal Willdenow or Acacia Seyal Delile, belonging to the leguminous plant Acacia. In particular, gum arabic obtained from Acacia Senegal Willdenow is preferred as the material. The origin of the gum arabic is not questioned and it may be derived from any production area. In addition, gum arabic can be obtained in the form of a desalted product, a massive product, a ball-shaped product, a coarsely pulverized product, granule, particle or powder (including spray-dried powder). In the present invention, regardless of the shape of these, any form can be used as the material for gum arabic to be treated in the present invention.

The plant proteoglycan of the present invention can be obtained by purifying gum arabic by subjecting same to an ion exchange resin treatment. In particular, a method in which gum arabic is dissolved in water to form an aqueous solution and the aqueous solution is subjected to an ion exchange resin treatment is preferred.

(Anion Exchange Resin)

In the present invention, low molecular weight impurities in gum arabic are removed by an anion exchange resin treatment, and the polymer content can be increased.

Examples of the resin matrix of the anion exchange resin include styrene-based resin matrix such as styrene-divinylbenzene and the like, (meth)acryl-based resin matrix, hydrogel-based resin matrix and the like. A styrene-based resin matrix is preferred from the aspect of the removal efficiency of low molecular weight impurities.

The matrix structure of anion exchange resin generally includes gel type and porous type. The gel type refers to those having only micropores, which are pores generated by swelling, and the porous type refers to those having macropores, which are physical pores that do not disappear even in a dry state, in addition to the micropores. From the aspect of removal efficiency of low molecular weight impurities, it is important that the anion exchange resin is of a porous type. In the present invention, the "porous type" is a concept including "high porous type" and "MR type (Macro-Reticular Type)". The "high porous type" refers to those having a structure having more developed pores than the porous type, and the MR type refers to an aggregate of gel fine beads.

Examples of the anion exchange resin form include powder form, spherical form, fiber form, membrane form, and the like.

The anion exchange resin generally includes strongly basic type I, strongly basic type II, and weakly basic. From the aspect of removal efficiency of low molecular weight impurities, it is important to use strongly basic type I type.

The strongly basic porous type I anion exchange resin to be used in the present invention may be manufactured by a known method or a commercially available product.

As the commercially available strongly basic porous type I anion exchange resin, for example, DIAION PA306, PA308, PA312, PA316, PA318 can be mentioned. As the strongly basic high porous type I anion exchange resin, HPA25, HPA25L (all above are manufactured by Mitsubishi Chemical Corporation) can be mentioned. As the strongly basic MR type I anion exchange resin, Amberlite IRA900J, IRA904, IRA958 (all above are manufactured by Organo Corporation) can be mentioned.

The anion exchange resin may be of a type in which a small particle size portion is cut, a type in which a large particle size portion is cut, a type in which a deodorizing treatment is performed, or a type in which an entanglement prevention treatment is performed. Examples of the counter ion of anion exchange resin include, but are not particularly limited to, hydroxide ion, chloride ion, hydrogen sulfite ion, and the like.

While the total exchange capacity of anion exchange resin is not particularly limited, from the aspect of the removal efficiency of low molecular weight impurities, it is preferably 0.1 meq/mL-3.0 meq/mL, more preferably 0.2 meq/mL-2.0 meq/mL, further preferably 0.3 meq/mL-1.5 meq/mL, particularly preferably 0.4 meq/mL-1.2 meq/mL. The amount of the anion exchange resin to be used is preferably 1.0 L-20 L, more preferably 2.0 L-15 L, and further preferably 4.0 L-10 L, per 1 kg of gum arabic, from the aspect of the removal efficiency of low molecular weight impurities.

(Cation Exchange Resin)

In the present invention, a treatment with a strongly acidic cation exchange resin can reduce the aldehyde compound content.

Examples of the resin matrix of the strongly acidic cation exchange resin include styrene-based resin matrix such as styrene-divinylbenzene and the like, and (meth)acryl-based resin matrix, and hydrogel-based resin matrix and the like. From the aspect of the aldehyde compound removal efficiency, a styrene-based resin matrix is preferred.

Examples of the matrix structure of the strongly acidic cation exchange resin include, but are not particularly limited to, a gel type and a porous type.

Examples of the strongly acidic cation exchange resin form include a powder form, a spherical form, a fiber form, a membrane form, and the like.

While the cation exchange resin includes those weakly acidic, strongly acidic ones are used from the aspect of the aldehyde compound removal efficiency.

The strongly acidic cation exchange resin to be used in the present invention may be manufactured by a known method or a commercially available product.

As the commercially available strongly acidic gel type cation exchange resin, for example, DIAION SK104, SK1B, SK1BH, SK110, SK112, UBK08, UBK510 can be mentioned. As the strongly acidic porous type cation exchange resin, PK208, PK212, PK216, PK220, PK228, RCP160M, HPK25 (all above are manufactured by Mitsubishi Chemical Corporation), Amberlite IR120B, IR124, 200CT, 252 (all above are manufactured by Organo Corporation) can be mentioned.

The cation exchange resin may be of a type in which a small particle size portion is cut, or a type in which a large particle size portion is cut.

Examples of the counter ion of cation exchange resin include, but are not particularly limited to, hydrogen ion, sodium ion, potassium ion, calcium ion, magnesium ion, barium ion, and the like.

The total exchange capacity of the strongly acidic cation exchange resin is not particularly limited. It is preferably 0.5 meg/mL-5.0 meq/mL, more preferably 1.0 meq/mL-4.0 meq/mL, further preferably 1.5 meq/mL-3.0 meq/mL, particularly preferably 1.8 meq/mL-2.5 meq/mL, from the aspect of the aldehyde compound removal efficiency.

The amount of the strongly acidic cation exchange resin to be used is preferably 0.05 L-0.50 L, more preferably 0.1 L-0.40 L, further preferably 0.15 L-0.30 L, per 1 kg of the gum arabic, from the aspect of the aldehyde compound removal efficiency.

In an ion exchange resin with reduced adsorption capacity due to the adsorption of impurities (strongly basic porous type I anion exchange resin and strongly acidic cation exchange resin), the adsorption capacity can be recovered by a known method, namely, chemical washing such as general acid or alkali washing, washing with an enzyme detergent, alcohol washing, surfactant washing, chelate washing, hypochlorous acid washing, hydrogen peroxide washing, and the like, physical washing such as brushing, backwashing operation, and the like.

As a method for treating a gum arabic aqueous solution with an ion exchange resin, any method that enables ion exchange between the ion exchange resin and the gum arabic aqueous solution, such as a batch method or a column method, may be used.

When a batch method is employed, a gum arabic aqueous solution may be treated with a mixture of an anion exchange resin and a cation exchange resin, or may be treated with each of the anion exchange resin and the cation exchange resin in any order.

On the other hand, when a column method is employed, a gum arabic aqueous solution may be treated by applying to a column filled with a mixture of an anion exchange resin and a cation exchange resin, or a gum arabic aqueous solution may be treated by applying to separate columns respectively filled with an anion exchange resin or a cation exchange resin in any order. In addition, a gum arabic aqueous solution may be treated by applying to respective columns filled with an anion exchange resin or a cation exchange resin and connected to each other in series.

The temperature of the gum arabic aqueous solution to be subjected to the ion exchange resin treatment is preferably not more than 60° C., more preferably 2° C.-60° C., more preferably 2° C.-50° C., and the concentration of the gum arabic aqueous solution is preferably not more than 40% (w/w), more preferably 0.5% (w/w)-40% (w/w), particularly preferably 1.0% (w/w)-20% (w/w). When the temperature of the gum arabic aqueous solution exceeds 60° C., gum arabic is denatured and aggregates may be generated during the treatment, or the temperature may exceed the heatproof temperature of the ion exchange resin. When the concentration of the gum arabic aqueous solution exceeds 40% (w/w), the viscosity of the solution becomes high to make the treatment difficult.

When the pH of the gum arabic aqueous solution is not less than 10, the gum arabic is decomposed. Thus, the pH of the gum arabic aqueous solution is preferably less than 10.

An aqueous solution containing plant proteoglycan can be obtained after a purification treatment using a strongly basic porous type I anion exchange resin and a strongly acidic cation exchange resin.

This aqueous solution containing plant proteoglycan may be further purified with a solvent containing any organic solvent or organic solvent. In addition, it may be further purified by an ion exchange resin treatment, a carrier treatment, a deodorization treatment, a desalting treatment, a membrane separation treatment, a pH adjustment treatment or the like.

When an aqueous solution containing plant proteoglycan is obtained, a membrane treatment and the like may be further performed for the purpose of desalting, sterilization, or the like.

A solid containing plant proteoglycan can also be obtained by subjecting the aqueous solution to a freeze-drying treatment, an evaporation-drying treatment, or the like.

The form of the plant proteoglycan of the present invention is not particularly limited, and may be any form such as liquid (e.g., aqueous solution and the like), massive product, ball-shaped product, coarsely pulverized product, granule, particle, powder and the like.

The plant proteoglycan of the present invention obtained as mentioned above has high physiological activity, particularly, a high cell proliferation activating action. In addition, it is derived from natural plant and has very high safety. Therefore, the plant proteoglycan of the present invention can be used as a cell proliferation promoter.

Such cell proliferation promoter of the present invention can be preferably utilized as a component to be blended with quasi-drugs, cosmetics, foods and the like, particularly as a cosmetic component (cosmetic).

The cell proliferation promoter of the present invention can be made into quasi-drug, cosmetic, food, or the like as it is or by adding general additives as necessary.

Examples of the additive include excipient, binder, disintegrant, lubricant, coating agent, base, solvent, solubilizing agent, solubilizer, suspending agent, dispersing agent, emulsifier, stabilizer, antioxidant, viscosity agent, preservative, pH adjuster, corrigent, flavor, colorant and the like. One or more kinds of these can be used.

EXAMPLE

The present invention is explained in more detail in the following by referring to Examples. The present invention not limited by the following Examples.

Example 1

Purification by Treatment with Strongly Basic Porous Type I Anion Exchange Resin and Strongly Acidic Cation Exchange Resin 50 g of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (1,250 g). This gum arabic aqueous solution, 170 g (251 mL) of strongly basic porous type I anion exchange resin "DIAION PA308" (manufactured by Mitsubishi Chemical Corporation, total exchange capacity=1.1 meq/mL) and 10 g (12 mL) of strongly acidic cation exchange resin "DIAION SK1BH" (manufactured by Mitsubishi Chemical Corporation, gel type, total exchange capacity=1.9 meq/mL) were placed in a tank, and the mixture was stirred for 3 hr with a stirring machine (liquid temperature=40±2° C.)

Then, the ion exchange resins were separated by filtration, and the filtrate was recovered. 1M NaOH was added to the filtrate to adjust the pH to 4.0. The aforementioned filtrate was freeze-dried to recover a solid (31.7 g) containing arabinogalactan protein.

SEC measurement of this solid was performed, and the weight average molecular weight was determined in the obtained chromatogram. FIG. 1 shows this chromatogram.

In addition, the total aldehyde content was determined using an aldehyde quantification kit.

Example 2

Purification by Treatment with Strongly Basic High Porous Type I Anion Exchange Resin and Strongly Acidic Cation Exchange Resin 3.6 kg of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (90 kg). This gum arabic aqueous solution, 17.24 kg (25 L) of strongly basic high porous type I anion exchange resin "DIAION HPA25L" (manufactured by Mitsubishi Chemical Corporation, total exchange capacity=0.7 meq/mL), and 0.7 kg (0.8 L) of strongly acidic cation exchange resin "DIAION SK1BH" (manufactured by Mitsubishi Chemical Corporation, gel type, total exchange capacity=1.9 meq/mL) were placed in a tank, and the mixture was stirred for 3 hr with a stirring machine (liquid temperature=20±2° C.)

Then, the ion exchange resins were separated by filtration, and the filtrate was recovered. 1M NaOH was added to the filtrate to adjust the pH to 4.0. The aforementioned filtrate was freeze-dried to recover a solid (2.2 kg) containing arabinogalactan protein.

SEC measurement of this solid was performed, and the weight average molecular weight was determined in the obtained chromatogram. FIG. 2 shows this chromatogram.

In addition, the total aldehyde content was determined using an aldehyde quantification kit.

Example 3

Purification by Treatment with Strongly Basic High Porous Type I Anion Exchange Resin and Strongly Acidic Cation Exchange Resin 50 g of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (1,250 g). This gum arabic aqueous solution, 102 g (150 mL) of strongly basic high porous type I anion exchange resin "DIAION HPA25L" (manufactured by Mitsubishi Chemical Corporation, total exchange capacity=0.7 meq/mL), and 5.0 g (6.0 mL) of strongly acidic cation exchange resin "DIAION SK1BH" (manufactured by Mitsubishi Chemical Corporation, gel type, total exchange capacity=1.9 meq/mL) were placed in a tank, and the mixture was stirred for 3 hr with a stirring machine (liquid temperature=40±2° C.)

Then, the ion exchange resins were separated by filtration, and the filtrate was recovered. 1M NaOH was added to the filtrate to adjust the pH to 4.0. The aforementioned filtrate was freeze-dried to recover a solid (37.9 g) containing arabinogalactan protein.

SEC measurement of this solid was performed, and the weight average molecular weight was determined in the obtained chromatogram. FIG. 3 shows this chromatogram.

In addition, the total aldehyde content was determined using an aldehyde quantification kit.

Comparative Example 1

Gum Arabic

Gum arabic (trade name: "Arabic Cole SS", Acacia Senegal species, manufactured by SAN-EI YAKUHIN BOEKI CO., LTD.) was subjected to SEC measurement, and the weight average molecular weight of the obtained chromatogram was determined. FIG. 4 shows this chromatogram.

In addition, the total aldehyde content was determined using an aldehyde quantification kit.

Comparative Example 2

Desalted Gum Arabic

Desalted gum arabic (trade name: "San Arabic", Acacia Senegal species, manufactured by SAN-EI YAKUHIN BOEKI CO., LTD.) was subjected to SEC measurement, and the weight average molecular weight of the obtained chromatogram was determined. FIG. 5 shows this chromatogram.

In addition, the total aldehyde content was determined using an aldehyde quantification kit.

Comparative Example

Purification by Treatment with Strongly Basic Porous Type I Anion Exchange Resin 50 g of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (1,250 g). This gum arabic aqueous solution and 170 g (251 mL) of strongly basic porous type I anion exchange resin "DIAION PA308" (manufactured by Mitsubishi Chemical Corporation, total exchange capacity=1.1 meq/mL) were placed in a tank, and the mixture was stirred for 3 hr with a stirring machine (liquid temperature=40±2° C.)

Then, the ion exchange resin was separated by filtration. The filtrate was recovered and freeze-dried to recover a solid (32.2 g) containing arabinogalactan protein.

SEC measurement of this solid was performed, and the weight average molecular weight was determined in the obtained chromatogram. FIG. 6 shows this chromatogram.

In addition, the total aldehyde content was determined using an aldehyde quantification kit.

Comparative Example 4

Purification by Treatment with Strongly Acidic Gel Type Cation Exchange Resin 50 g of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (1,250 g). This gum arabic aqueous solution and 10 g (12 mL) of strongly acidic cation exchange resin "DIAION SK1BH" (manufactured by Mitsubishi Chemical Corporation, gel type, total exchange capacity=1.9 meq/mL) were placed in a tank, and the mixture was stirred for 3 hr with a stirring machine (liquid temperature=40±2° C.)

Then, the ion exchange resin was separated by filtration, and the filtrate was recovered. 1M NaOH was added to the filtrate to adjust the pH to 4.0. The aforementioned filtrate was freeze-dried to recover a solid (49.7 g) containing arabinogalactan protein.

SEC measurement of this solid was performed, and the weight average molecular weight was determined in the obtained chromatogram. FIG. 7 shows this chromatogram.

In addition, the total aldehyde content was determined using an aldehyde quantification kit.

Comparative Example 5

Purification by Treatment with Strongly Basic Gel Type I Anion Exchange Resin and Strongly Acidic Cation Exchange Resin 50 g of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (1,250 g). This gum arabic aqueous solution, 170 g (251 mL) of strongly basic gel type I anion exchange resin "DIAION SA10A" (manufactured by Mitsubishi Chemical Corporation, total exchange capacity=1.4 meq/mL) and 10 g (12 mL) of strongly acidic cation exchange resin "DIAION SK1BH" (manufactured by Mitsubishi Chemical Corporation, gel type, total exchange capacity=1.9 meq/mL) were placed in a tank, and the mixture was stirred for 3 hr with a stirring machine (liquid temperature=40±2° C.)

Then, the ion exchange resins were separated by filtration, and the filtrate was recovered. 1M NaOH was added to the filtrate to adjust the pH to 4.0. The aforementioned filtrate was freeze-dried to recover a solid (49.5 g) containing arabinogalactan protein.

SEC measurement of this solid was performed, and the weight average molecular weight was determined in the obtained chromatogram.

In addition, the total aldehyde content was determined using an aldehyde quantification kit.

Comparative Example 6

Purification by Treatment with Strongly Basic Porous Type II Anion Exchange Resin and Strongly Acidic Cation Exchange Resin 50 g of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (1,250 g). This gum arabic aqueous solution, 170 g (251 mL) of strongly basic porous type II anion exchange resin "DIAION PA408" (manufactured by Mitsubishi Chemical Corporation, total exchange capacity=1.0 meq/mL) and 10 g (12 mL) of strongly acidic cation exchange resin "DIAION SK1BH" (manufactured by Mitsubishi Chemical Corporation, gel type, total exchange capacity=1.9 meq/mL) were placed in a tank, and the mixture was stirred for 3 hr with a stirring machine (liquid temperature=40±2° C.).

Then, the ion exchange resins were separated by filtration, and the filtrate was recovered. 1M NaOH was added to the filtrate to adjust the pH to 4.0. The aforementioned filtrate was freeze-dried to recover a solid (49.2 g) containing arabinogalactan protein.

SEC measurement of this solid was performed, and the weight average molecular weight was determined in the obtained chromatogram.

In addition, the total aldehyde content was determined using an aldehyde quantification kit.

Comparative Example 7

Purification by Treatment with Strongly Basic Porous Type I Anion Exchange Resin and Weakly Acidic Cation Exchange Resin 50 g of gum arabic (trade name: "Arabic Cole SS", Acacia Senegal species, manufactured by SAN-EI YAKUHIN BOEKI CO., LTD.) was dissolved in ion exchange water to prepare a 4.0% (w/w) gum arabic aqueous solution (1,250 g). This gum arabic aqueous solution, 170 g (251 mL) of strongly basic porous type I anion exchange resin "DIAION WK10" (manufactured by Mitsubishi Chemical Corporation, total exchange capacity=1.1 meq/mL) and 10 g (12 mL) of weakly acidic cation exchange resin "DIAION WK10" (manufactured by Mitsubishi Chemical Corporation, methacryl-based, total exchange capacity=2.6 meq/mL) were placed in a tank, and the mixture was stirred for 3 hr with a stirring machine (liquid temperature=40±2° C.)

Then, the ion exchange resins were separated by filtration, and the filtrate was recovered. 1M NaOH was added to the filtrate to adjust the pH to 4.0. The aforementioned filtrate was freeze-dried to recover a solid (32.5 g) containing arabinogalactan protein.

SEC measurement of this solid was performed, and the weight average molecular weight was determined in the obtained chromatogram.

In addition, the total aldehyde content was determined using an aldehyde quantification kit.

Comparative Example 8

Modified Gum Arabic 2.0 g of gum arabic (trade name: "Arabic Cole SS", Acacia Senegal species, manufactured by SAN-EI YAKUHIN BOEKI CO., LTD.) was placed in an oven set to 110° C. and heated for 24 hr. After heating, a solid (1.9 g) was recovered.

SEC measurement of this solid was performed, and the weight average molecular weight was determined in the obtained chromatogram. FIG. 8 shows this chromatogram.

In addition, the total aldehyde content was determined using an aldehyde quantification kit.

Comparative Example 9

Animal Proteoglycan

Animal proteoglycan (manufactured by Wako Pure Chemical Industries, Ltd.) was subjected to SEC measurement, and the weight average molecular weight was determined on the obtained chromatogram. In addition, the total aldehyde content was determined using an aldehyde quantification kit.

[Evaluation Test]

Solids containing arabinogalactan proteins obtained in the above-mentioned Examples 1-3 and Comparative Examples 3-7, the gum arabic of Comparative Example 1, the desalted gum arabic of Comparative Example 2, the modified gum arabic of Comparative Example 8 and the animal proteoglycan of Comparative Example 9 as samples were subjected to the following tests.

<Cell Proliferation Activity Test>

Using HuMedia-KG2 medium (manufactured by KURABO) containing 10 µg/mL insulin and 0.5 µg/mL hydrocortisone, human normal epidermal keratinocyte (manufactured by KURABO) was seeded in a 96-well culture microplate by 100 µL at a concentration of $2 \times 10^4$ cells/mL, and cultured for 24 hr under the conditions of 5% (v/v) $CO_2$, 37° C. Thereafter, each sample was added to the final concentration of 250 µg/mL, the aforementioned medium after removing insoluble materials with a 0.20 µm cellulose acetate membrane filter was added by 100 µL each, and the cells were cultured for 96 hr.

Then, viable cell count was measured with a BrdU (5-bromo-2'-deoxyuridine) chemiluminescent kit (manufactured by Abcam K.K.), and an epidermal cell proliferation promoting action was analyzed when the viable cell count without addition of the sample was 100.

<Moisture Retention Test>

Aqueous solutions containing 2.0% (w/w) each of respective samples were prepared, and each aqueous solution was added dropwise to a petri dish by 100 µL. The petri dish was stood in an environment of room temperature=25±1° C., humidity=20±1% RH for 60 min, and the weight of the sample aqueous solution after 60 min was divided by the weight of the initial sample aqueous solution to determine the proportion (%).

<Sensory Test>

Aqueous solutions containing 1.0% (w/w) of respective samples were applied to the inner part of the forearm of 20 professional panelists, and the sense of use was sensory-evaluated according to the following evaluation criteria. The average value of the evaluation results was calculated by rounding to integers.

(1) Sticky Feeling

3: not sticky, 2: rather not sticky, 1: sticky, 0: strongly sticky (2) Smell

3: odorless, 2: slight odor, 1: odor, 0: strong odor

The following Table 1 shows the parameters (weight average molecular weight, total aldehyde content) of all Examples and all Comparative Examples, and the results of the above-mentioned evaluation tests.

TABLE 1

| | parameter | | | | sensory test | |
|---|---|---|---|---|---|---|
| sample | weight average molecular weight (×10,000) | total aldehyde content (μmol equivalent/g) | cell proliferation activity test | moisture retention test | sticky feeling | odor |
| Example 1: Purification by treatment with strongly basic porous type I anion exchange resin and strongly acidic cation exchange resin | 143 | 0.9 | 148 | 68 | 3 | 3 |
| Example 2: Purification by treatment with strongly basic high porous type I anion exchange resin and strongly acidic cation exchange resin | 174 | 0.6 | 166 | 72 | 3 | 3 |
| Example 3: Purification by treatment with strongly basic high porous type I anion exchange resin and strongly acidic cation exchange resin | 107 | 1.9 | 137 | 66 | 3 | 3 |
| Comparative Example 1: Gum arabic | 84 | 3.3 | 81 | 42 | 3 | 1 |
| Comparative Example 2: Desalted gum arabic | 86 | 2.5 | 84 | 42 | 3 | 1 |
| Comparative Example 3: Purification by treatment with strongly basic porous type I anion exchange resin | 142 | 2.6 | 82 | 63 | 3 | 0 |
| Comparative Example 4: Purification by treatment with strongly acidic gel type cation exchange resin | 85 | 1.9 | 88 | 43 | 3 | 3 |
| Comparative Example 5: Purification by treatment with strongly basic gel type I anion exchange resin and strongly acidic cation exchange resin | 84 | 1.9 | 88 | 42 | 3 | 3 |
| Comparative Example 6: Purification by treatment with strongly basic porous type II anion exchange resin and strongly acidic cation exchange resin | 84 | 1.9 | 88 | 42 | 3 | 3 |
| Comparative Example 7: Purification by treatment with strongly basic porous type I anion exchange resin and weakly acidic cation exchange resin | 142 | 3.2 | 83 | 63 | 3 | 0 |
| Comparative Example 8: Modified gum arabic | 399 | 5.9 | 61 | 44 | 0 | 0 |
| Comparative Example 9: Animal proteoglycan | 61 | 1 | 130 | 56 | 3 | 3 |

As shown in Table 1, the solids containing arabinogalactan protein and obtained in Examples 1 to 3 all had a weight average molecular weight of 900,000 to 3,500,000 and a total aldehyde content of not more than 2.0 μmol equivalent/g. It was evaluated that these show cell proliferation activity and moisture retention equal to or higher than those of animal proteoglycan (Comparative Example 9), and that no stickiness or odor was observed.

The gum arabic of Comparative Example 1, the desalted gum arabic of Comparative Example 2, and the solids obtained in Comparative Examples 4-6 had a weight average molecular weight of less than 900,000, and the modified gum arabic of Comparative Example 8 had a weight average molecular weight exceeding 3,500,000. In addition, the gum arabic of Comparative Example 1, the desalted gum arabic of Comparative Example 2, the solids obtained in Comparative Examples 3 and 7, and the modified gum arabic of Comparative Example 8 had a total aldehyde content exceeding 2.0 μmol equivalent/g. These were not found to have cell proliferation activity and moisture retention equal to or higher than those of animal proteoglycan (Comparative Example 9), the gum arabic of Comparative Example 1, the desalted gum arabic of Comparative Example 2, the solids obtained in Comparative Examples 3 and 7 were evaluated to have odor or strong odor, and the modified gum arabic of Comparative Example 8 was evaluated to have a sticky feeling and strong odor.

INDUSTRIAL APPLICABILITY

As described in detail above, according to the present invention, a plant proteoglycan having physiological activity equal to or higher than that of known animal proteoglycan and capable of exhibiting a superior moisturizing effect and a cell proliferation promoting effect on human skin can be provided.

The plant proteoglycan of the present invention is useful as a cell proliferation promoter, and can be preferably utilized for quasi-drugs, cosmetics, foods and the like.

The invention claimed is:

1. A method for obtaining a plant proteoglycan from gum arabic, wherein the method comprises
   (A) a step of preparing an aqueous solution of gum arabic having a concentration of 0.5% (w/w)-40% (w/w), wherein the gum arabic is obtained from a trunk or branch of an Acacia Senegal Willdenow or Acacia Seyal Delile plant, and
   (B) a step of subjecting the aqueous solution of gum arabic to a strongly basic porous type I anion exchange resin and a strongly acidic cation exchange resin, thereby obtaining the plant proteoglycan having a weight average molecular weight of 900,000-3,500,000, measured by size exclusion chromatography, and having a total aldehyde content of not more than 2.0 μmol equivalent/g.

* * * * *